(12) United States Patent
Karamanoglu et al.

(10) Patent No.: US 8,706,235 B2
(45) Date of Patent: Apr. 22, 2014

(54) TRANSVENOUS METHOD TO INDUCE RESPIRATION (75) Inventors: Mustafa Karamanoglu, Fridley, MN (US); Vincent E. Splett, Apple Valley, MN (US); Nancy J. Rakow, Oak Grove, MN (US); Linnea R. Lentz, Stacy, MN (US)

(73) Assignee: Medtronic, Inc., Minneapolis, MN (US)

( * ) Notice: Subject to any disclaimer, the term of this patent is extended or adjusted under 35 U.S.C. 154(b) by 108 days.

(21) Appl. No.: 13/192,116

(22) Filed: Jul. 27, 2011

(65) Prior Publication Data
US 2013/0030496 A1    Jan. 31, 2013

(51) Int. Cl.
*A61N 1/00* (2006.01)
(52) U.S. Cl.
USPC ................................. 607/42; 607/46; 607/62
(58) Field of Classification Search
USPC .................................. 607/27, 28, 42, 46, 62
See application file for complete search history.

(56) References Cited

U.S. PATENT DOCUMENTS

| | | | |
|---|---|---|---|
| 4,901,725 A | 2/1990 | Nappholz | |
| 5,056,519 A | 10/1991 | Vince | |
| 5,117,824 A | 6/1992 | Keimel | |
| 5,265,604 A | 11/1993 | Vince | |
| 5,524,632 A | 6/1996 | Stein | |
| 5,824,021 A | 10/1998 | Rise | |
| 5,824,029 A | 10/1998 | Weijand | |
| 5,911,218 A | 6/1999 | DiMarco | |
| 6,006,134 A * | 12/1999 | Hill et al. | 607/9 |
| 6,076,015 A | 6/2000 | Hartley | |
| 6,463,327 B1 | 10/2002 | Lurie | |
| 7,277,757 B2 | 10/2007 | Casavant | |
| 7,363,085 B1 | 4/2008 | Benser et al. | |
| 7,363,086 B1 | 4/2008 | Koh | |
| 7,672,729 B2 | 3/2010 | Koh | |
| 7,672,733 B2 | 3/2010 | Zhou et al. | |
| 2005/0085865 A1 | 4/2005 | Tehrani | |
| 2006/0116737 A1* | 6/2006 | Libbus | 607/44 |
| 2006/0276848 A1 | 12/2006 | Min | |
| 2007/0118183 A1* | 5/2007 | Gelfand et al. | 607/42 |
| 2007/0255379 A1 | 11/2007 | Williams et al. | |
| 2008/0161878 A1 | 7/2008 | Tehrani | |
| 2008/0208282 A1 | 8/2008 | Gelfand | |
| 2008/0288015 A1 | 11/2008 | Tehrani | |
| 2009/0036947 A1 | 2/2009 | Westlund | |

* cited by examiner

*Primary Examiner* — Michael Kahelin
*Assistant Examiner* — Mallika D Fairchild
(74) *Attorney, Agent, or Firm* — Carol F. Barry (57) ABSTRACT

A system and method for delivering a nerve stimulation therapy determines whether a cardiac EGM signal can be sensed by a bipolar pair of electrodes selected from a number of electrodes positioned for stimulating a nerve. In response to not being able to sense a cardiac signal using the bipolar pair, stimulation of the nerve using a selected pair of the electrodes is enabled.

14 Claims, 9 Drawing Sheets

TRANSVENOUS METHOD TO INDUCE RESPIRATION

TECHNICAL FIELD

The disclosure relates generally to implantable medical devices and, more particularly, to a method and apparatus for transvenously inducing respiration.

BACKGROUND

Stimulation of the right and left phrenic nerves to cause contraction of the diaphragm has been proposed for treating respiratory insufficiency, e.g. in paralysis, apnea, or other respiratory conditions. Phrenic nerve stimulation may be achieved using nerve electrodes implanted in proximity to the phrenic nerve in an open surgical approach. A less invasive approach for implanting electrodes positioned in proximity to a phrenic nerve is a transvenous approach. Electrodes are implanted transvenously, for example in a subclavian vein or the superior vena cava (SVC), such that the phrenic nerve is stimulated through the wall of the vein.

Stimulation of a phrenic nerve using a transvenous approach, however, can include the risk of inadvertent cardiac stimulation. Stimulation of the heart could induce arrhythmias. A need remains for phrenic nerve stimulation methods and associated apparatus for effectively delivering phrenic nerve stimulation for respiration therapies.

DETAILED DESCRIPTION

In the following description, references are made to illustrative embodiments. It is understood that other embodiments may be utilized without departing from the scope of the disclosure.

Figure 1:
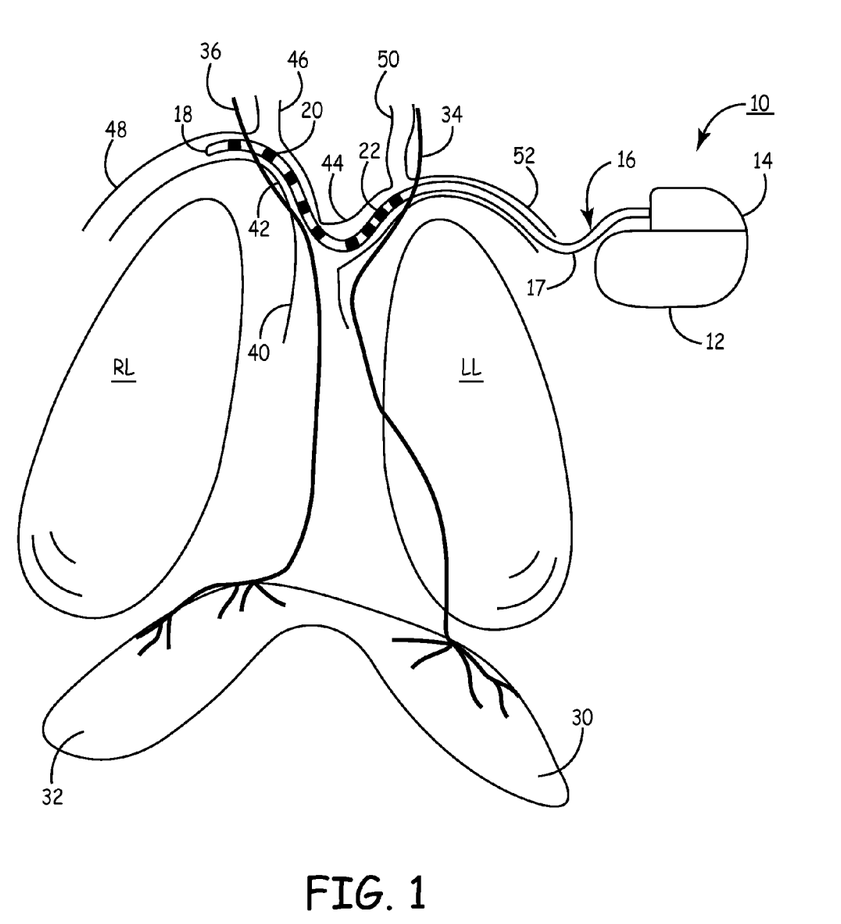
FIG. 1 is a schematic view of an implantable medical device (IMD) system for delivering phrenic nerve stimulation according to one embodiment.

FIG. 1 is a schematic view of an implantable medical device (IMD) system for delivering phrenic nerve stimulation. IMD 10 includes a housing 12 enclosing electronic circuitry (not shown) included in IMD 10 and a connector block 14 having a connector bore for receiving at least one medical electrical lead 16 and providing electrical connection between electrodes carried by lead 16 and IMD internal electronic circuitry.

In FIG. 1, the left phrenic nerve 34 and the right phrenic nerve 36 are shown innervating the respective left diaphragm 30 and right diaphragm 32. The anatomical locations of the left phrenic nerve 34, the right phrenic nerve 36 and other anatomical structures shown schematically in the drawings presented herein are intended to be illustrative of the approximate and relative locations of such structures. These structures are not necessarily shown in exact anatomical scale or location. Left phrenic nerve 34 is shown schematically to extend in close proximity to the left internal jugular vein (LJV) 50, the left subclavian vein (LSV) 52, and the left innominate vein (LIV) 44, also referred to as the left brachiocephalic vein.

The anatomical location of the right phrenic nerve 36 is shown schematically to extend in close proximity to the right internal jugular vein (RJV) 46, the right subclavian vein (RSV) 48, the right innominate vein (RIV) 42 (also referred to as the right brachiocephalic vein), and the superior vena cava (SVC) 40.

Lead 16 is a multipolar lead carrying proximal electrodes 22 spaced proximally from distal electrodes 20, positioned at or near the distal end 18 of lead 16. In one embodiment, at least one proximal bipolar pair of electrodes is provided for stimulating the left phrenic nerve 34 and at least one distal bipolar pair of electrodes is provide for stimulating the right phrenic nerve 36. In various embodiments, two or more electrodes may be spaced apart along the lead body, near the distal tip 18 of lead 16, from which at least one pair of electrodes is selected for delivering stimulation to the right phrenic nerve 36. Additionally, two or more electrodes may be positioned along spaced apart locations proximally from the distal electrodes 20 from which at least one pair of electrodes is selected for delivering stimulation to the left phrenic nerve 34.

Lead 16 includes an elongated lead body 17, which may have a diameter in the range of approximately 2 French to 8 French, and typically approximately 4 French to approximately 6 French. The lead body carries the electrodes 20 and 22 which are electrically coupled to electrically insulated conductors extending from respective individual electrodes 20 and 22 to a proximal connector assembly adapted for connection to IMD connector block 14. Lead 16 may be provided with a fixation element for fixing the position of the lead once a desired implant location is identified. Exemplary leads that can be useful for the present disclosure include U.S. Pat. Nos. 5,922,014, 5,628,778, 4,497,326, 5,443,492, or 7,860,580 such that electrodes are added and/or spaced apart in a manner similar to that disclosed in the figures of the present application, all of which are incorporated by reference in their entirety. Additional lead and electrode configurations that may be adapted for use with the present disclosure by adjusting lead shape, length, electrode number and/or electrode to effectively provide phrenic nerve stimulation as described herein are generally disclosed in U.S. Pat. Nos. 7,031,777, 6,968,237, and U.S. Publication No. 2009/0270729, all of which are incorporated herein by reference in their entirety.

In one embodiment, distal tip 18 of lead 16 is advanced to a location along the RIV 42 and further along the RSV 48 or the RJV 46 to position distal electrodes 20 in operative relation to right phrenic nerve 36 for delivering stimulation pulses to nerve 36 to activate the right diaphragm 32. The proximal electrodes 22 may be appropriately spaced from distal electrodes 20 such that proximal electrodes 22 are positioned along the LIV 44 and/or along the junction of the LSV 52 and LJV 50 for delivering stimulation pulses to the left phrenic nerve 34 to activate the left diaphragm 30.

In various embodiments, lead 16 may carry four or more electrodes spaced at selected distances to provide at least one pair near a distal lead tip 18 for right phrenic nerve stimulation and at least one pair more proximally for left phrenic nerve stimulation. In other embodiments, lead 16 may carry multiple electrodes spaced equally along a portion of the body of lead 16 such that any pair may be selected for right phrenic nerve stimulation and any pair may be selected for left phrenic nerve stimulation based on the relative locations of the electrodes from the nerves. Furthermore, it is recognized that in some embodiments, stimulation of only one of the right or left phrenic nerve may be required and an appropriate number and location of electrodes may be provided along lead 16 for such purposes.

Figure 2:
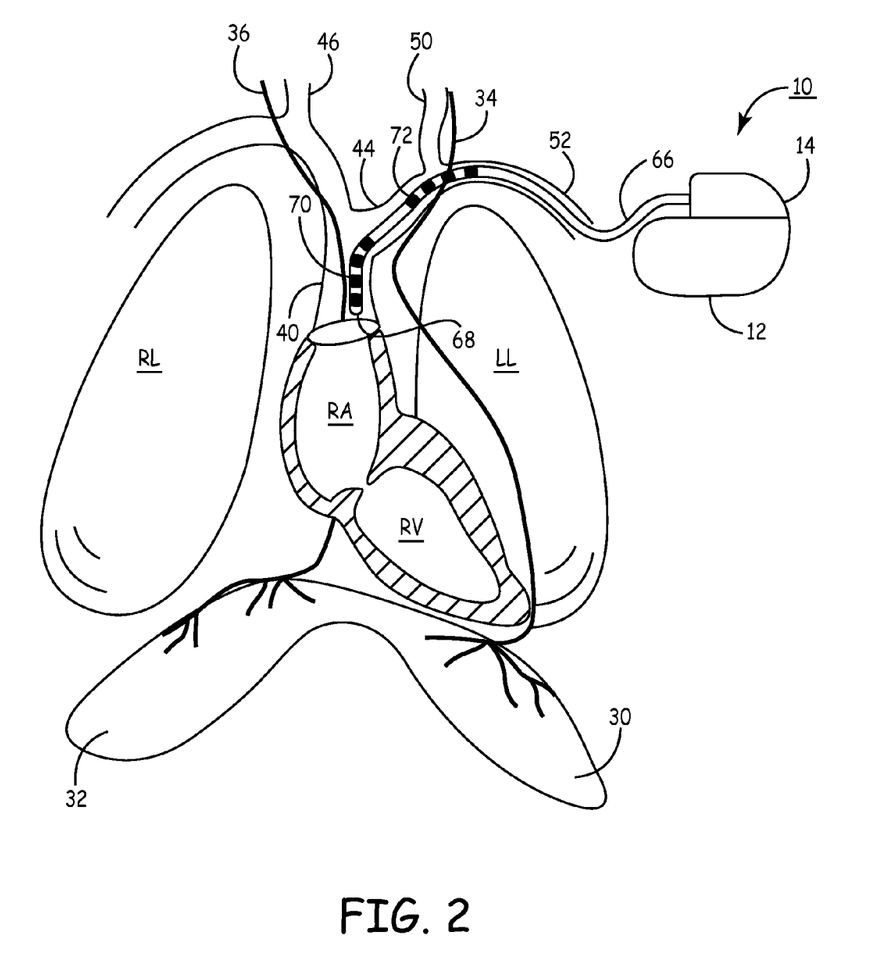
FIG. 2 is a schematic view of an IMD system for delivering phrenic nerve stimulation according to an alternative embodiment.

FIG. 2 is a schematic view of an IMD system for delivering phrenic nerve stimulation according to an alternative embodiment. In FIG. 2, the right atrium (RA) and the right ventricle (RV) are shown schematically in a partially cut-away view. The right phrenic nerve 36 extends posteriorly along the SVC 40, the RA and the inferior vena cava (IVC) (not shown in FIG. 2). The left phrenic nerve 34 normally extends along a left lateral wall of the left ventricle (not shown). The SVC 40 enters the RA. A lead 66 is coupled to IMD 10 via connector block 14. Lead 66 carries multiple electrodes, which may be spaced apart into a plurality of distal electrodes 70 located near distal lead tip 68 and a plurality of proximal electrodes 72. The distal tip 68 of lead 66 is advanced into SVC 40 to position distal electrodes 70 for stimulating the right phrenic nerve 36. The proximal electrodes 72 are used to stimulate the left phrenic nerve 34, e.g. along the LIV 44 or junction of the LJV 50 and LSV 52.

Figure 3:
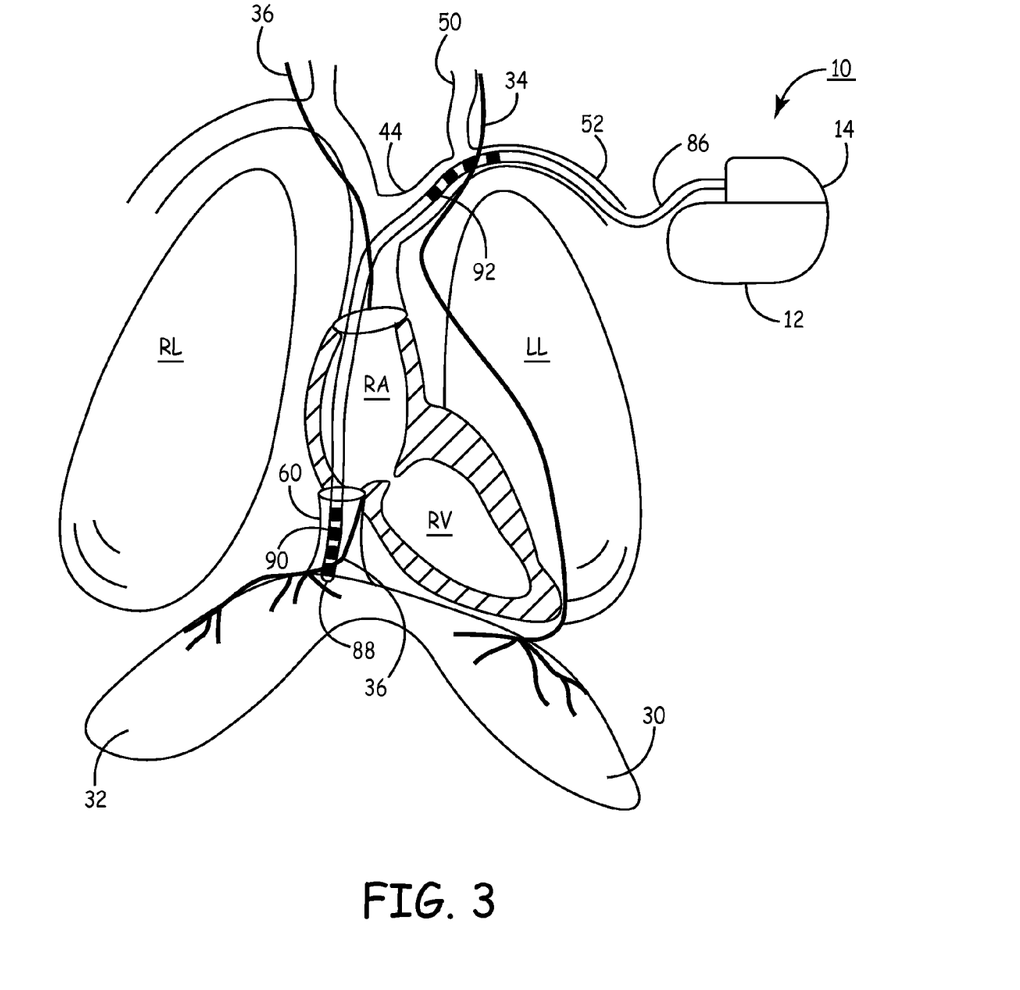
FIG. 3 is a schematic view of an IMD system for delivering phrenic nerve stimulation according to another alternative embodiment.

FIG. 3 is a schematic view of an IMD system for delivering phrenic nerve stimulation according to another alternative embodiment. In FIG. 3, the inferior vena cava (IVC) 60, which empties into the RA, is shown schematically. In this embodiment, lead 86 extends from IMD connector block 14 to the IVC 60 to position electrodes 90, carried by lead 86 at or near distal lead tip 88, along the IVC 60 adjacent the right phrenic nerve 36 near the level of the diaphragm, e.g. approximately at the height of the eighth thoracic vertebra (T8) (not shown). Proximal electrodes 92 are positioned proximally along lead 86 for positioning along the LIV 44 or junction of the LJV 50 and LSV 52 for providing stimulation to the left phrenic nerve 34.

Electrodes used for stimulating the right phrenic nerve and electrodes used for stimulating the left phrenic nerve are shown configured along a common lead in FIGS. 1 through 3. In alternative embodiments it is contemplated that two leads, one for stimulating the left and one for stimulating the right phrenic nerve, may be provided separately. Whether provided as a single lead or two leads, either lead placed along the venous locations shown may become dislodged into the right atrium or located near enough to the heart to cause inadvertent capture of the cardiac tissue directly or nerves that innervate cardiac tissue, such as the vagus nerve or other sympathetic nerves. Methods described herein provide an implant and therapy delivery technique to minimize the risk of inadvertent cardiac stimulation, or cardiac nerve stimulation, during a phrenic nerve stimulation therapy.

The housing 12 of IMD 10 may be provided as an indifferent electrode for use in combination with any of the lead-based electrodes shown in FIGS. 1 through 3 for some monitoring purposes. As will be further described below, the electrodes included in an IMD system for delivering a phrenic nerve stimulation therapy may additionally be used for sensing cardiac electrical signals (EGM) signals and for measuring thoracic impedance signals. In some embodiments, the housing 12 may provide an indifferent electrode for sensing EGM signals, delivering a drive current during thoracic impedance measurements or used in a measurement pair for monitoring thoracic impedance.

It is further recognized that additional leads and electrodes may be included in an IMD system capable of delivering transvenous phrenic nerve stimulation. For example, IMD 10 may be coupled to cardiac leads, which may be subcutaneous leads, transvenous leads positioned in or along a heart chamber, or epicardial leads. IMD 10 may incorporate sensing electrodes along housing 12. IMD 10 may be provided specifically for delivering phrenic nerve stimulation (with associated monitoring of sensed signals for controlling the phrenic nerve stimulation) or may include other therapy delivery capabilities such as cardiac pacing (e.g. for bradycardia pacing, cardiac resynchronization therapy, or anti-tachycardia pacing) cardioversion/defibrillation shocks, drug delivery or the like. As such, the IMD system may include other leads, electrodes and/or catheters not shown in FIGS. 1 through 3 as needed for other IMD functions. In some embodiments, electrodes used for delivering phrenic nerve stimulation could be carried by leads that additionally carry cardiac pacing, sensing and/or defibrillation electrodes. In other embodiments, sensing electrodes carried by cardiac leads may be used for sensing EGM signals to detect inadvertent cardiac capture or cardiac nerve stimulation for use in controlling a phrenic nerve stimulation therapy and during positioning of the phrenic nerve stimulation electrodes.

In FIGS. 1 through 3, IMD 10 is shown in a left pectoral position such that it is the distal electrodes, e.g., electrodes 20, 70, or 90 that are positioned in operative relation to the right phrenic nerve 36 and the proximal electrodes, e.g., electrodes 22, 72, or 92, that are positioned in operative relation to the left phrenic nerve 34. Depending on the implanted configuration, a phrenic nerve stimulation lead, e.g. lead 16 or 66, may be positioned entering a vein from a right venous approach such that it is the distal electrodes 20 or 70, that are positioned for left phrenic nerve stimulation and the proximal electrodes 22 or 72 that are positioned for right phrenic nerve stimulation. For example, IMD 10 may be implanted in a pocket along a right pectoral position, along a right or left abdominal position, centrally, or other implant location. The IMD implant location may determine whether it is the proximal electrodes or the distal electrodes that are positioned for stimulating the right or the left phrenic nerves, when the electrodes are all carried by a single phrenic nerve stimulation lead.

For example, a right-sided implantation of IMD 10 could include distal electrodes positioned along the LIV 44 for left phrenic nerve stimulation and proximal electrodes positioned for right phrenic nerve stimulation along the RIV 42 or junction of the RSV 48 and RJV 46. As such, in the methods described hereafter, testing and monitoring for EGM sensing, cardiac capture, and/or non-phrenic nerve capture may involve testing of proximal and/or distal electrodes depending on the particular implant configuration being used.

Figure 4:
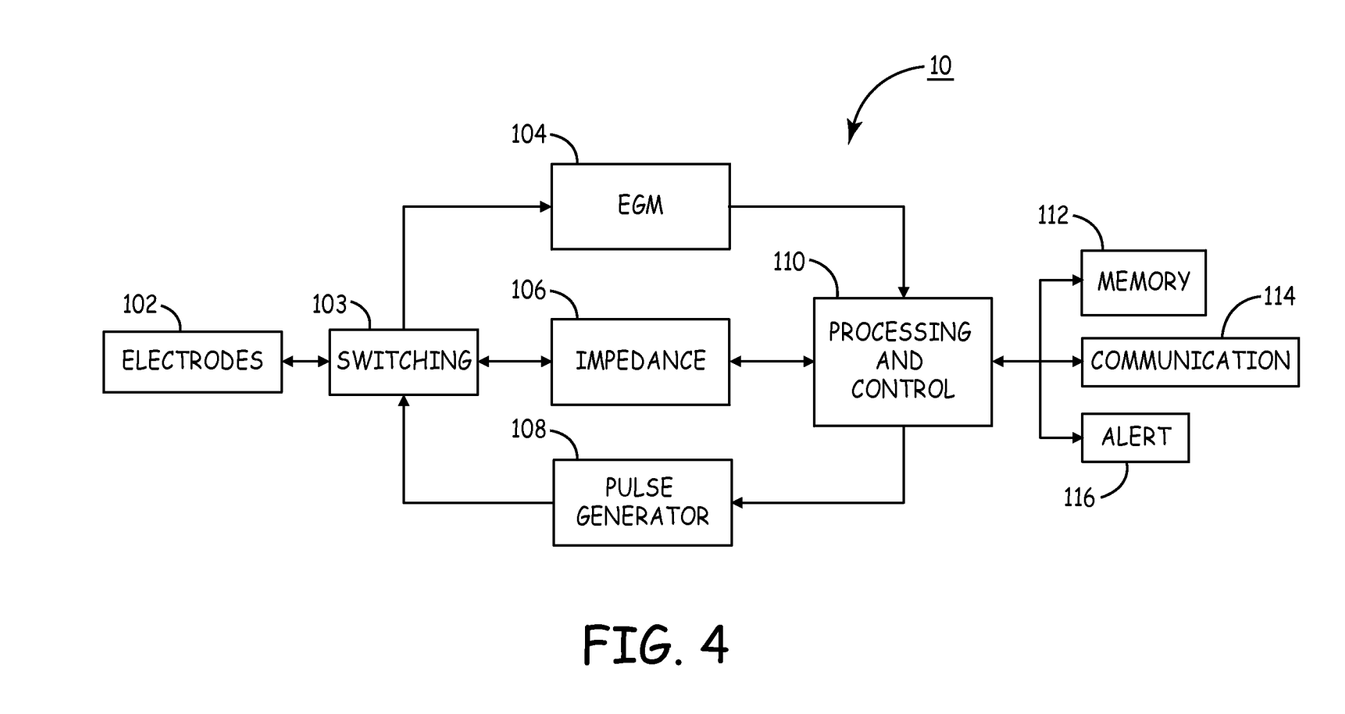
FIG. 4 is a functional block diagram of an IMD that may be associated with any of the leads and implant locations shown in FIGS. 1 through 3.

FIG. 4 is a functional block diagram of an IMD that may include any of the leads and implant locations shown in FIGS. 1 through 3. Electrodes 102 are coupled to EGM sensing 104, impedance sensing 106, and pulse generator 108 via switching circuitry 103. Electrodes 102 may correspond to any of the electrodes shown in FIGS. 1 through 3 or other electrodes carried along one or more leads for delivering phrenic nerve stimulation. Electrodes 102 may further include other electrodes available along the IMD housing and any other subcutaneous or cardiac leads coupled to IMD 10.

Electrodes 102 are selected via switching circuitry 103 for coupling to EGM sensing circuitry 104 to sense for the presence of EGM signals on phrenic nerve stimulation electrodes and/or for evidence of inadvertent capture of the heart or cardiac nerves. Electrodes 102 may also be selected in impedance signal drive current and measurement pairs via switching circuitry 103 for monitoring thoracic impedance by impedance monitoring circuitry 106. Electrodes 102 are further selected via switching circuitry 103 for delivering phrenic nerve stimulation pulses generated by pulse generator 108.

EGM sensing circuitry 104 is provided for sensing for the presence of an EGM signal on phrenic nerve stimulation electrodes during implantation and during nerve stimulation therapy delivery for detecting a potential risk for cardiac capture. If the electrodes selected for phrenic nerve stimulation are located in close proximity of the heart, nerve stimulation pulses may inadvertently be delivered to the heart, potentially capturing myocardial tissue and inducing arrhythmias. If an EGM signal can be sensed using the electrodes selected for phrenic nerve stimulation, the electrodes may be too close or within the heart. As such, determining that an EGM signal can be sensed using phrenic nerve stimulation electrodes indicates a risk of unintentional cardiac stimulation.

Additionally or alternatively, EGM sensing circuitry 104 is provided for sensing cardiac signals for detecting capture of the heart or a cardiac nerve (e.g. vagus nerve or other sympathetic nerves which may affect heart rate) during phrenic nerve stimulation. In this case, the EGM sensing circuitry may be coupled to any of the phrenic nerve lead electrodes, cardiac electrodes, or subcutaneous electrodes positioned for sensing cardiac EGM or ECG signals such that cardiac events (P-waves or R-waves) may be sensed and used to determine if phrenic nerve stimulation is affecting the rate of these sensed cardiac events.

The impedance sensing circuitry 106 includes drive current circuitry and impedance measurement circuitry for monitoring thoracic impedance. The thoracic impedance measurements can be used to select optimal electrodes and stimulation parameters for achieving a desired effect on respiration caused by phrenic nerve stimulation. It is recognized that other types of physiological sensors, such as pressure sensors, EMG electrodes or accelerometers may be used for sensing a respiratory response to phrenic nerve stimulation and may be substituted or used in addition to thoracic impedance monitoring.

Processing and control 110 receives signals from EGM sensing 104 and impedance sensing circuitry 106. In response to received signals processing and control 110 controls delivery of phrenic nerve stimulation by pulse generator 108. Processing and control 110 may be embodied as a programmable microprocessor and associated memory 112. Received signals may additionally include user command signals received by communication circuitry 114 from an external programming device and used to program processing and control 110. Processing and control 110 may be implemented as any combination of an application specific integrated circuit (ASIC), an electronic circuit, a processor (shared, dedicated, or group) and memory that execute one or more software or firmware programs, a combinational logic circuit, or other suitable components that provide the described functionality.

Memory 112 stores data associated with the monitored EGM (or ECG) and impedance signals. Data may be transmitted to an external device by communication circuit 114, which typically includes wireless transmitting and receiving circuitry and an associated antenna for bidirectional communication with an external device. Processing and control 110 may generate reports or alerts that are transmitted by communication circuitry 114.

Alert circuitry 116 may be provided for generating a patient alert signal to notify the patient or a clinician of a condition warranting medical attention. In one embodiment, an alert is generated in response to sensing an EGM signal using the phrenic nerve stimulation electrodes and/or detecting inadvertent capture of the heart or cardiac nerves. EGM sensing or inadvertent capture of the heart or cardiac nerves indicates possible lead dislodgement and risk of cardiac stimulation that may adversely affect heart rate or induce arrhythmias. The patient may be alerted via an audible sound, perceptible vibration, IMD pocket stimulation, or the like and be advised to seek medical attention upon perceiving an alert signal.

Figure 5:
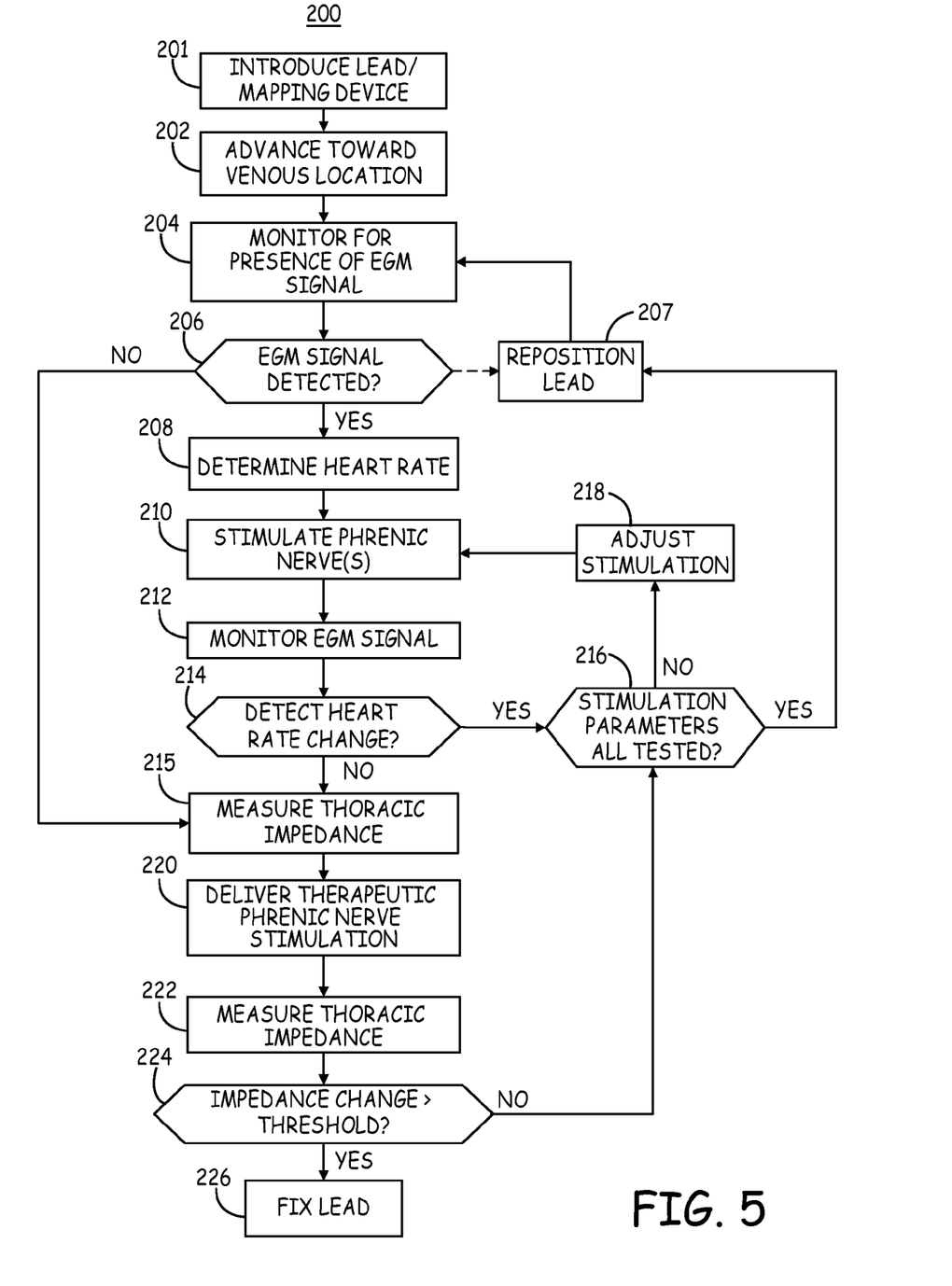
FIG. 5 is a flow chart of a method for positioning a lead for phrenic nerve stimulation according to one embodiment.

FIG. 5 is a flow chart 200 of a method for positioning a lead for phrenic nerve stimulation according to one embodiment. At block 201, the phrenic nerve stimulation lead, or a mapping device, is introduced via a venous puncture and vein introducer device. The lead or mapping device is advanced toward a targeted venous location at block 202. Lead or device advancement may be facilitated with the use of fluoroscopy or other imaging method to visualize the location of the lead or mapping device along the venous vasculature.

In one or more embodiments, a mapping device is provided in the form of a guide or delivery catheter that includes electrodes that can be used for sensing EGM signals. The electrodes may additionally be used for delivering stimulation pulses to test phrenic nerve stimulation. The electrodes may be located at positions along the catheter that correspond to electrode locations on a phrenic nerve stimulation lead. Such a mapping device may be considered a "phrenic nerve stimulation lead" because it carries electrodes that can be used for testing phrenic nerve stimulation but is intended for temporary use for mapping and for guiding a chronically implantable phrenic nerve stimulation lead to a desired implant location.

Advancement of a lead toward a venous location may include the use of a guide catheter and/or guide wire. The nerve stimulation lead may be an "over the wire" type lead that includes an open lumen for receiving a guide wire, over which the lead is advanced for placement at a desired venous location. Alternatively, the lead may be sized to be advanced within a lumen of a guide catheter that is then retracted for monitoring signals and testing phrenic nerve stimulation.

Electrodes carried by the phrenic nerve stimulation lead (or mapping device) are coupled to an EGM sense amplifier for observing whether an EGM signal can be sensed by any of the electrodes carried by the lead during its advancement, at block 204. The EGM sense amplifier may be included in EGM sensing circuitry in the IMD. The lead may be coupled directly to the IMD during the implantation procedure with EGM sensing circuitry output transmitted to an external device for display and observation by a clinician. Alternatively, the lead (or mapping device) may be coupled to external test apparatus that includes EGM sensing circuitry and cardiac signal display.

When the lead carries multiple electrodes, the electrodes may be selected sequentially in bipolar pairs for determining if an EGM signal can be sensed using any bipolar pair carried by the lead. For example, switching circuitry may be provided for selecting which electrodes are being tested. Switching may be performed manually through a user command. The user may then observe a telemetered signal sensed by the selected electrodes to determine if an EGM signal is being sensed.

Alternatively, switching circuitry may be controlled automatically by the IMD or external test device controller to cycle through different electrode combinations. Automatic detection of an EGM signal by the IMD or an external test apparatus may occur upon sensing regularly occurring R-waves or P-waves or identifying an EGM signal morphology. An EGM signal detection alert may then be generated automatically.

Alternatively, the most distal bipolar pair may be monitored as the lead or catheter is advanced since the most distal pair may be the first pair likely to pick up an EGM signal as the lead or catheter is generally advanced from a venous puncture site toward the heart to a desired venous location.

Detection of an EGM signal at block 206 may be based on sensing P-waves or R-waves using a sense amplifier and auto-adjusting threshold, for example as generally described in U.S. Pat. No. 5,117,824 (Keimel, et al.), hereby incorporated herein by reference in its entirety. The rate of sensed events may be compared to an expected range of possible heart rates to indicate regular R-wave or P-wave sensing. Additionally or alternatively, a morphology analysis may be performed at decision block 206 to compare the morphology of an unknown sensed signal to a known EGM signal morphology template to determine if the unknown morphology approximately matches the EGM signal morphology. The displayed signal may be inspected by a user instead of or in addition to an automatic signal analysis for detecting the presence of an EGM signal sensed by the phrenic nerve stimulation electrodes.

In some embodiments, detection of an EGM signal at block 206 may include a signal amplitude criterion. For example, R-wave sensing at or above a predefined sensing threshold or R-wave peak amplitudes exceeding a predefined amplitude may be required before lead repositioning is necessary. Low level signals may indicate that the electrodes are far enough from the heart that cardiac capture is not expected to occur.

A dashed arrow to block 207 indicates the option of repositioning the lead if an EGM signal is sensed. The lead or mapping device may be repositioned at block 207 until no sensing of an EGM signal is present (block 206). If no EGM signal is sensed, the electrodes may be assumed to be far enough from the heart to avoid cardiac capture. In one embodiment, stimulation of the phrenic nerve using the selected bipolar pair at the current implant position is enabled in response to no EGM signal being sensed by a selected pair of electrodes. The process advances directly from block 206 to block 215 to measure thoracic impedance and evaluate a respiratory response to the phrenic nerve stimulation using the selected electrodes.

In addition to or alternatively to monitoring for EGM signal sensing, detection of inadvertent capture of the heart or cardiac nerves may be performed during the implantation procedure. If an EGM signal is sensed at block 206, a pre-stimulation heart rate is optionally determined at block 208 for detecting changes in heart rate due to inadvertent capture of the heart or cardiac nerves.

At block 210, electrical stimulation pulses are delivered to the right, left or both phrenic nerves, individually or synchronously. In some embodiments, a single stimulation pulse is delivered at block 210 at a rate higher than an intrinsic heart rate. The timing of stimulation pulses may be controlled to avoid delivering a stimulation pulse during the cardiac vulnerable period.

The EGM (or an ECG) signal is monitored at block 212. Any available electrodes may be used for monitoring a heart rate signal to detect a change in heart rate due to phrenic nerve stimulation. If the heart rate changes as determined at block 214 when phrenic nerve stimulation is initiated, capture of the heart or cardiac nerves is likely. For example, if the heart rate increases or matches the rate of single stimulation pulses being delivered to the phrenic nerve(s), as determined at block 214, the nerve stimulation pulses are capturing and pacing the heart.

Phrenic nerve stimulation pulses may be delivered at block 210 at a maximum stimulation amplitude and/or pulse width, i.e. a maximum pulse energy, to determine if this high pulse energy causes a heart rate change. If not, it can be assumed that the phrenic nerve(s) can be safely stimulated using the selected electrodes without causing inadvertent cardiac capture or cardiac nerve stimulation.

In other embodiments, the stimulation delivered at block 210 may be a "therapeutic" stimulation pattern of pulse trains delivered at a desired respiration rate to achieve a respiratory response. The heart rate may be monitored to see if these pulse trains cause any unintended affect on heart rate.

If a cardiac nerve is being stimulated above its stimulation threshold, the heart rate may decrease. For example, vagal nerve stimulation causes a decreased heart rate response. As such, detection of a heart rate change determined at block 214 may include detecting an increase or a decrease in heart rate, which may or may not be a rate that matches the phrenic nerve stimulation rate.

If a change in heart rate is detected at block 214 that indicates capture of the heart and/or a cardiac nerve, a stimulation parameter may be adjusted at block 218. Different stimulation parameter settings may be tested until no heart rate change is detected or until a selected number of possible stimulation parameter settings or combinations have been tested (block 216). Stimulation parameters that may be adjusted at block 218 include, but are not limited to, pulse amplitude, pulse number, pulse train frequency, selected stimulation electrodes, and electrode polarity.

If no change in heart rate is detected at block 214, phrenic nerve stimulation may be delivered using the selected electrodes. Before starting a therapeutic level of phrenic nerve stimulation, a thoracic impedance measurement may be made at block 215 to determine a baseline respiration measurement when phrenic nerve stimulation is not being delivered. The thoracic impedance measurement may be made using any available electrodes.

Multiple impedance measurements may be made across different measurement vectors. For example electrodes that provide an impedance measurement substantially across or within the right thoracic cavity may be obtained to assess stimulation of the right phrenic nerve and electrodes that provide an impedance measurement substantially across or within the left thoracic cavity may be obtained to assess stimulation of the left phrenic nerve. Alternatively or additionally to right- and/or left-sided impedance measurements, impedance measurements corresponding to a measurement volume that includes portions of both the right and left thoracic cavity may be obtained. The measurements taken at block 215 are pre-stimulation measurements taken to establish a baseline respiration measurement before phrenic nerve stimulation therapy is initiated.

In the illustrative embodiments, thoracic impedance measurements are described herein for assessing the effectiveness of phrenic nerve stimulation. Other measurements correlated to respiration or diaphragmatic activation may be substituted or used in addition to the thoracic impedance measurements.

Other measurements may include, but are not limited to, air flow measurements, diaphragmatic EMG signal measurements, fluoroscopic or other imaging techniques, manual palpation, accelerometer or other motion sensor measurements, and thoracic pressure measurements.

If single pulses or other test parameter settings were used at block 210 to first detect a heart rate change in response to phrenic nerve stimulation, the phrenic nerve stimulation may be adjusted at block 220 to a therapeutic phrenic nerve stimulation pattern. For example, if single pulses were delivered at block 212, the phrenic nerve stimulation may be adjusted to pulse trains delivered at an intended respiratory rate at block 220.

A thoracic impedance measurement is made at block 222 to measure a respiratory response to the phrenic nerve stimulation. The impedance measurement performed at block 215 prior to phrenic nerve stimulation is repeated at block 222 using the same measurement vector(s). The thoracic impedance signal will be a cyclic signal that decreases to a minimum during expiration as the lungs empty and increases to a maximum during inhalation as the lungs fill with air producing a higher thoracic impedance. A thoracic impedance measurement may be an average impedance, a maximum impedance, a maximum to minimum difference (peak-to-peak difference), a slope, an area, or other measurement correlated to respired volume, any of which may be averaged over one or more respiration cycles and taken alone or in any combination.

The pre-stimulation impedance measurement and the impedance measurement obtained during phrenic nerve stimulation therapy are compared at block 224 to determine if a change in the impedance measurement is at least greater than a desired threshold level of improvement. The impedance change may be measured as a difference or ratio of the pre-stimulation impedance measurement and the measurement obtained during stimulation. A threshold change may be a percentage increase over the pre-stimulation measurement. The threshold comparison used at block 224 may be tailored to individual patients and will depend on the particular needs and therapy objectives for a given patient.

If the impedance change is not acceptable at block 224, other stimulation parameters may be tested by adjusting the stimulation at block 218. Stimulation adjustments may include, but are not limited to, pulse amplitude, pulse number, pulse train frequency, selected stimulation electrodes, and electrode polarity.

If all electrode combinations available and a maximum number of stimulation pulse train control parameters (e.g., different settings and combinations of settings for pulse amplitude, pulse frequency, and pulse number) have been tested, as determined at decision block 216, the lead may be repositioned by returning to block 207. If the lead is repositioned, the presence of EGM signal sensing and/or detection of heart rate change due to phrenic nerve stimulation are checked for again by looping back to block 204 or back to block 208. The process of verifying a lead position that does not result in EGM signal sensing and/or cardiac capture or heart rate change and does result in a desired improvement in the impedance measurement (or other measurement correlated to respiration) is repeated.

Once the desired improvement is achieved (block 224), the phrenic nerve stimulation lead is fixed in place at block 226. Lead fixation may involve suturing a proximal portion of the lead or the use of lead fixation members. After lead fixation, the lead may be coupled to the IMD and a phrenic nerve stimulation therapy enabled.

Flow chart 200 presents a lead implantation procedure according to one particular embodiment. It is recognized that the procedures described in conjunction with flow chart 200 may be performed in a different order than described here or some procedures may be omitted in a method for determining an acceptable location for a phrenic nerve lead and selecting phrenic nerve stimulation electrodes and stimulation parameters. For example, the method may include sensing for EGM signals present on phrenic nerve lead electrodes or detecting a heart rate change using any available electrodes, or both. Furthermore, it is contemplated that monitoring of cardiac signals may be performed throughout the processes shown by blocks 220 through 224 when measurements and necessary adjustments are being made to obtain a desired respiratory response in order to determine if phrenic nerve stimulation begins to capture the heart or a cardiac nerve causing a change in heart rate during this process.

Figure 6A:
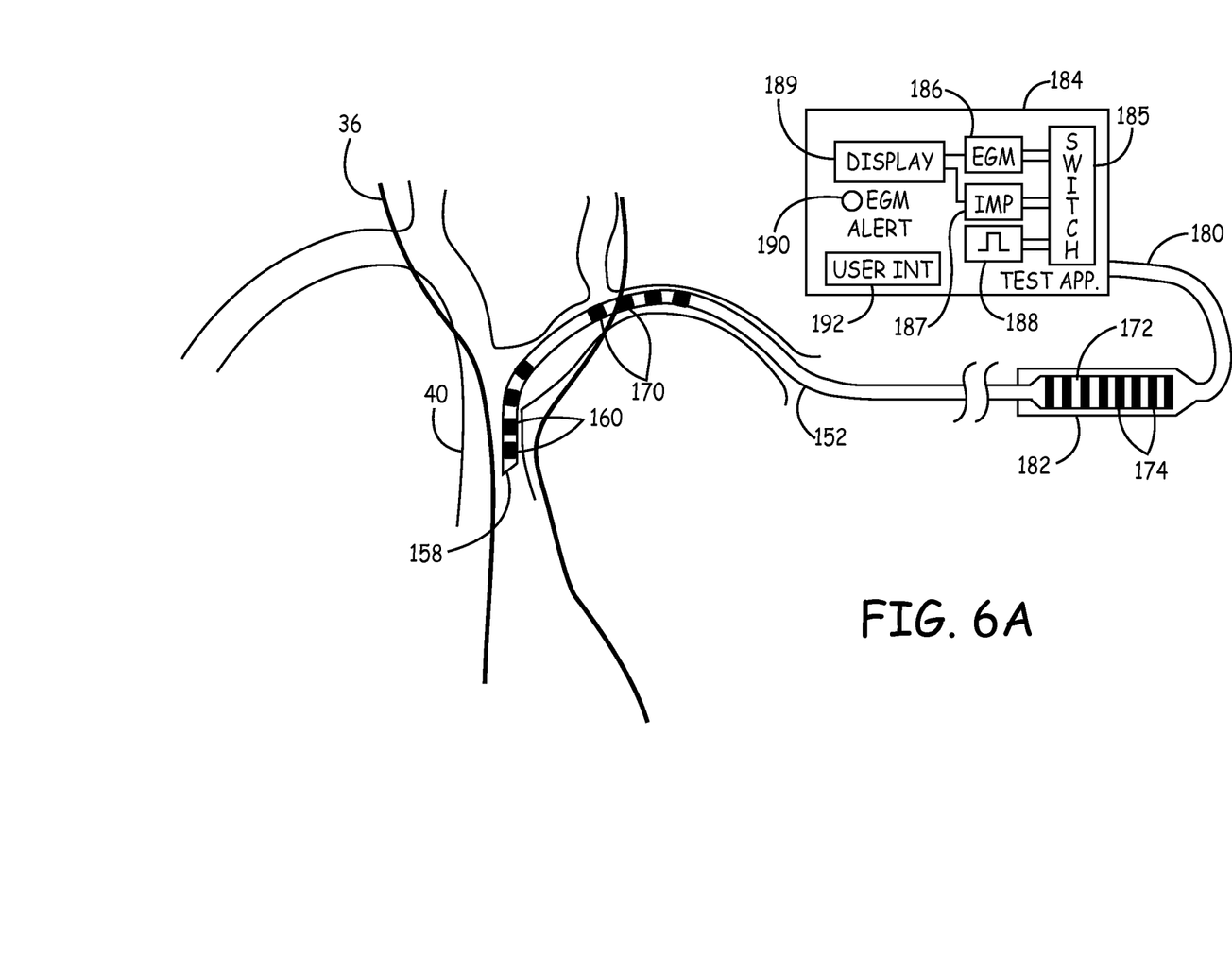
FIGS. 6A and 6B are schematic diagrams of an implantation procedure for positioning an IMD system for phrenic nerve stimulation.
Figure 6B:
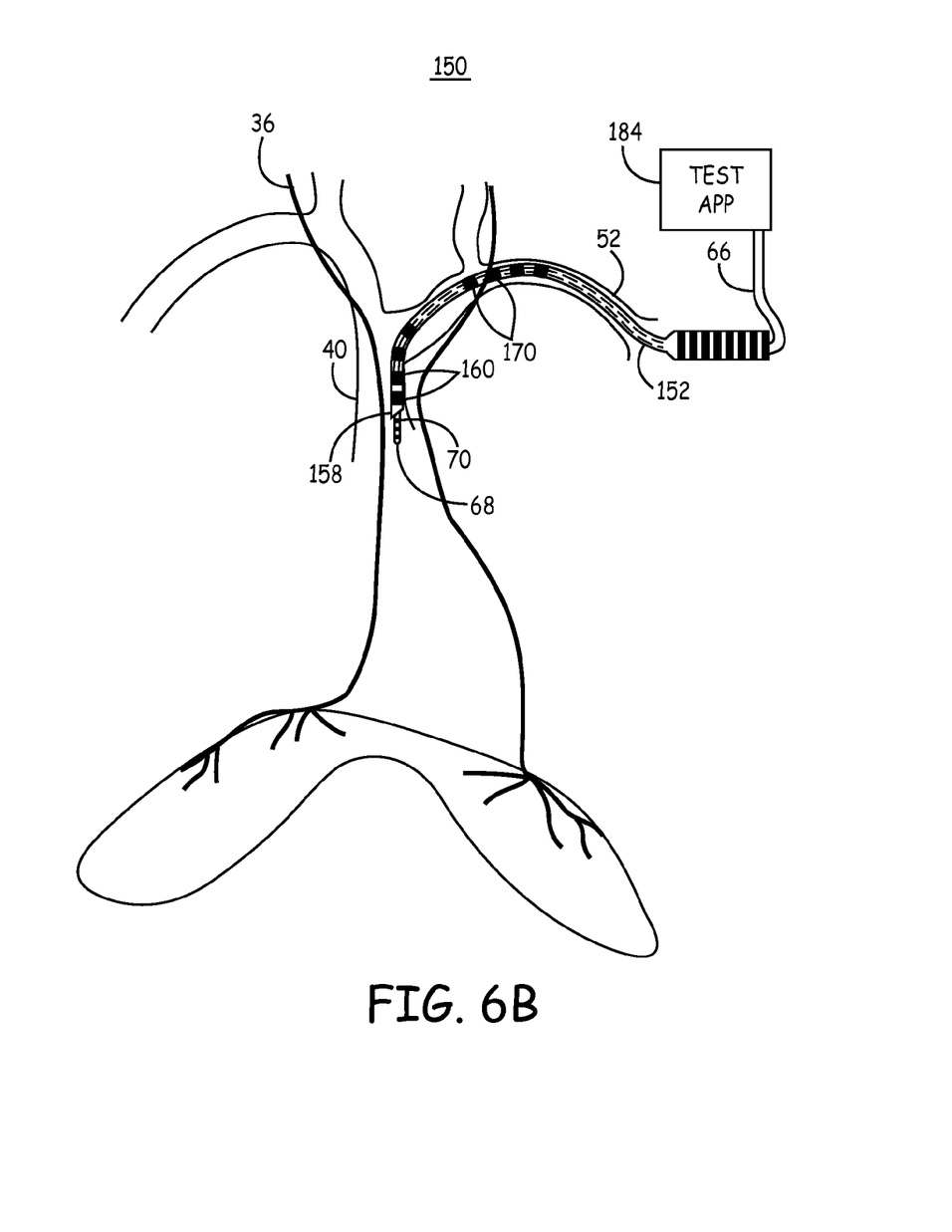

FIGS. 6A and 6B are schematic diagrams of an implantation procedure for positioning an IMD system for phrenic nerve stimulation. In FIG. 6A, a delivery and mapping catheter 152 is advanced to position a distal catheter end 158 in the SVC 40. Catheter 152 is provided with multiple distal electrodes 160 (four shown in FIG. 6A) and multiple proximal electrodes 170 (four shown). The multiple distal and proximal electrodes 160 and 170 may correspond to the electrode configuration of a chronically implantable phrenic nerve stimulation lead. Alternatively, catheter 152 may be provided only with distal electrodes 160 since the distal portion of catheter 152 (and a subsequently implanted lead) is the most likely portion to fall within or near enough to the patient's heart to result in inadvertent cardiac capture.

Catheter 152 includes a proximal connector assembly 172 including connectors 174 that enable either direct connection to a test apparatus 184, or cable 180. A cable may be provided with a female connector portion 182 for receiving connector assembly 172. Alternatively, catheter 152 may be configured for direct coupling to an IMD 10. Test apparatus 184 may be provided as an external testing apparatus used in conjunction with the delivery and mapping catheter 152 during the implantation procedure for identifying a desired lead implant site before a chronically implantable phrenic nerve stimulation lead and associated IMD are implanted. It is recognized that in other embodiments the phrenic nerve stimulation lead may be implanted and tested directly for identifying a desired implant site without the use of electrodes on a delivery catheter. The nerve stimulation lead may be coupled to the test apparatus 184 as shown here or directly to the IMD during implant procedure testing.

Test apparatus 184 may include automatic switching circuitry 185 that selectively couples distal electrodes 160 and optionally the proximal electrodes 170 to EGM sensing circuitry 186 for monitoring for the presence of an EGM signal on any of the electrodes 160 and 170. In one embodiment, only the distal most pair of electrodes 160, nearest distal end 158, is coupled to EGM sensing circuitry during advancement of catheter 152 for detecting an EGM signal. If an EGM signal is detected automatically by EGM detection circuitry 186, an EGM alert 190, which may include an LED and/or audible sound, may be activated to notify a clinician. The EGM signal may be displayed on display 189 for verification of the presence of an EGM signal by the clinician.

If stimulation of the right phrenic nerve is to be delivered from a SVC location, verification of no EGM sensing or no capture of the heart or cardiac nerves along all or at least some of electrodes 160 may be performed. Once verified, activation of the right phrenic nerve may be verified by delivering stimulation pulses from pulse generator 188 via switching circuitry 185 using various combination of selected electrodes 160 and a default supra-threshold stimulation pulse amplitude.

Any of electrodes 160 and 170 may be used for delivering a drive current and measuring a resulting impedance signal by coupling the drive and measurement electrode pairs to impedance measuring circuitry 187. Examples of thoracic impedance measurement methods that can be used for monitoring a respiration signal are generally described in U.S. Pat. No. 4,901,725 (Nappholz), U.S. Pat. No. 6,076,015 (Hartley), and U.S. Pat. No. 5,824,029 (Weijand, et al), all of which are hereby incorporated herein by reference in their entirety. User commands for selecting electrodes for delivering stimulation, selecting impedance measuring electrodes, and selecting stimulation parameters may be entered via a user interface 192. Alternatively, a programmed test sequence may be performed automatically with impedance measurement results for different test conditions displayed on display 189.

Referring now to FIG. 6B, once an acceptable implant location has been identified, the nerve stimulation lead 66 may be advanced through the delivery catheter 152 until the lead distal end 68 reaches the catheter distal tip 158. Lead distal end 68 is not advanced more distally than the catheter distal tip 158. Catheter 152 is shown partially withdrawn over lead 66 to expose the distal electrodes 70 of lead 66. A proximal connector assembly (not shown) of lead 66 may be coupled to test apparatus 184, or directly to IMD 10, to allow verification of successful capture of right phrenic nerve 36 by distal electrodes 70 with no EGM sensing and/or no change in heart rate during phrenic nerve stimulation. The lead 66 may be disconnected from apparatus 184 or IMD 10 to allow complete withdrawal of catheter 152 from lead 66. Further testing of the most effective electrodes and stimulation parameters may be performed. Lead 66 may then be fixed in place and coupled to IMD 10 for chronic implantation.

In alternative embodiments, testing of a phrenic nerve lead or a corresponding delivery catheter intended for a implantation site along the RIV 42 or junction of the RSV 48 and RJV 46, as generally shown in FIG. 1, may involve monitoring for EGM sensing and/or cardiac capture using a most proximal electrode pair of distal electrodes 20 and a most distal electrode pair of proximal electrodes 22 to verify that none of these electrodes, if selected for delivering nerve stimulation, risk inadvertent cardiac capture or stimulation of cardiac nerves.

It is intended that at least the electrodes in closest proximity to the patient's heart are monitored for the presence of an EGM signal or tested for causing a heart rate change due to phrenic nerve stimulation during implantation, and again during therapy delivery as will be described below. Depending on the implant configuration, the electrodes in closest proximity to the heart may be electrodes included in the proximal electrodes 22, 72, 92 and 170 of respective leads 16, 66, 86 and catheter 152 and/or distal electrodes 20, 70, 90, and 160 of respective leads 16, 66, 86, and catheter 152 (FIGS. 1-3 and FIG. 6A). It is further recognized that the electrodes in closest proximity to the heart (or a cardiac nerve) may change during advancement of the lead or catheter to a desired location. Accordingly, the electrodes being monitored for the presence of an EGM signal or tested for capturing the heart or a cardiac nerve may be changed based on the location of the electrodes relative to the heart or cardiac nerves.

For example, as the lead 16 shown in FIG. 1 is advanced to the right innominate vein, initially a distal most electrode pair out of distal electrodes 20 may be monitored for EGM sensing. As the lead is advanced further, a more proximal pair of electrodes 20 may be monitored for EGM sensing. As the lead is advanced even further, a distal pair of proximal electrodes 22 may be monitored for EGM sensing. Once positioned at a desired implant site, the most proximal of the distal electrodes 20 and the most distal of the proximal electrodes 22 may be monitored to detect the presence of an EGM signal and/or cardiac capture due to dislodgement of the lead 16 toward or into the patient's heart.

Figure 7:
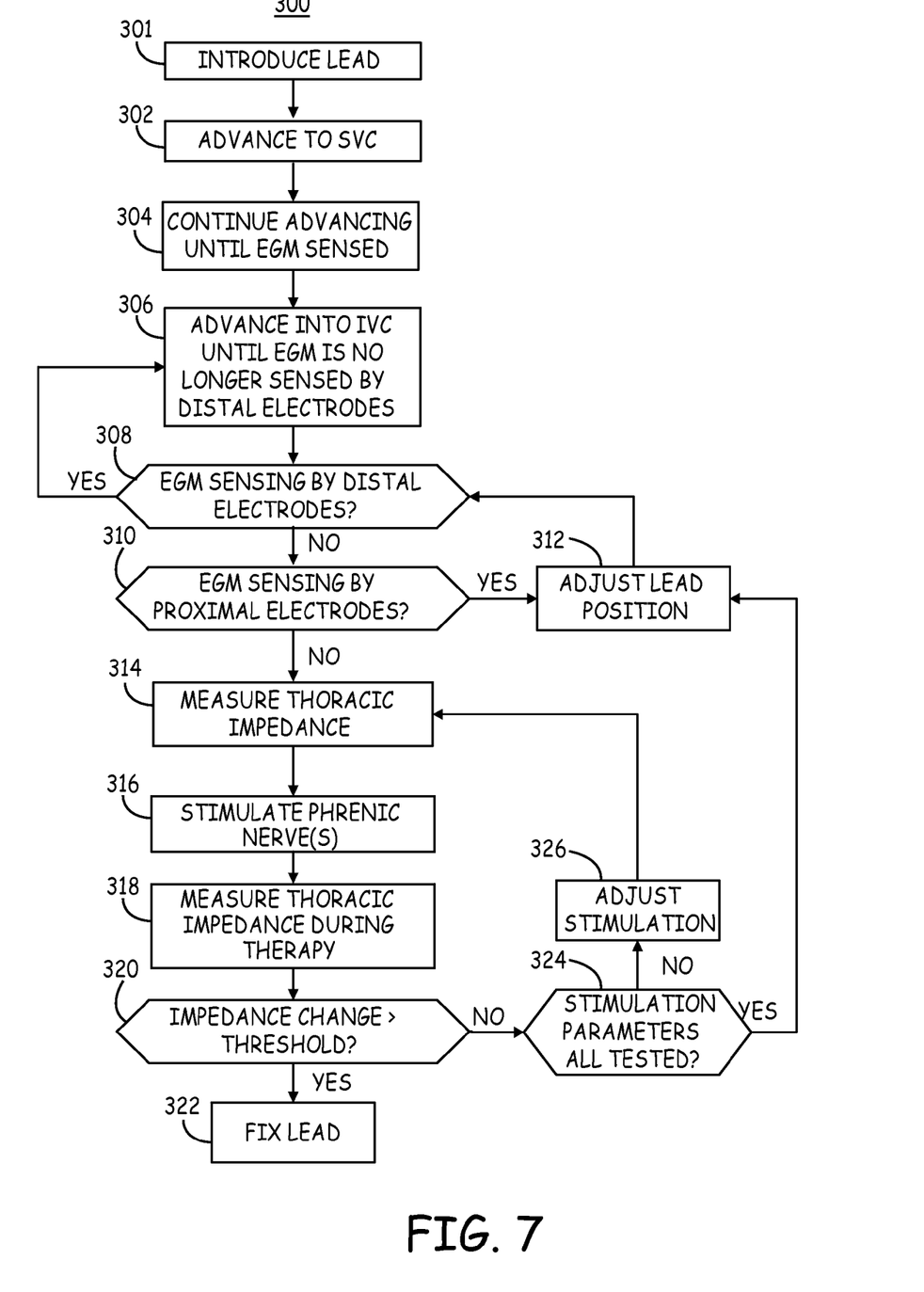
FIG. 7 is a flow chart of a method for implanting a phrenic nerve stimulation lead according to another embodiment.

FIG. 7 is a flow chart 300 of a method for implanting a phrenic nerve stimulation lead according to another embodiment. The method shown by flow chart 300 will be described with reference to lead 86 of FIG. 3, with a targeted implant location of the distal lead end 88 in the IVC near the level of the diaphragm. At block 301, a phrenic nerve stimulation lead, (or a delivery catheter having electrodes spaced apart at locations corresponding to electrode locations on the lead) is introduced through a venous access site. The lead (or catheter) is advanced to the SVC at block 302.

During continued advancement of the lead (or catheter), optionally with the use of fluoroscopy or other imaging, the most distal electrode pair is monitored to detect an EGM signal at block 304. Once the EGM signal is sensed indicating that the distal lead or catheter end is in the RA, the lead (or catheter) is advanced further at block 306 until the EGM is no longer sensed, indicating the distal end has been advanced out of the RA into the IVC.

Additionally at block 306, the EGM signal monitoring may be switched from a most distal pair of distal electrodes 90 to a most proximal pair of the distal electrodes 90. Once the distal end 88 of lead 86 is located in the IVC, some distal electrodes 90 may remain near the heart depending on the number and spacing of the electrodes. As such, it may be desirable to advance lead 86 further distally until the most proximal electrode pair of distal electrodes 90 can no longer sense an EGM signal.

Once an EGM signal is no longer sensed by distal electrodes 90, or at least by a most distal pair of electrodes to enable safe right phrenic nerve stimulation with minimized risk of inadvertent cardiac capture, EGM signal monitoring may be performed at block 310 to determine if an EGM signal can be sensed using any of proximal electrodes 92. In one embodiment, the most distal pair of proximal electrodes 92 is tested for EGM sensing. If the most distal pair does not sense an EGM signal, proximal electrodes 92 are most likely far enough from the heart to avoid inadvertent cardiac capture. In another embodiment, a most proximal pair of electrodes 92 is tested. If at least one proximal pair of electrodes 92 does not sense an EGM signal, that pair can be selected for stimulation of the left phrenic nerve.

If EGM sensing by any (or selected ones) of proximal electrodes 92 is present, the lead position is adjusted at block 312. Lead adjustment typically involves retraction of the lead to a more proximal location to move proximal electrodes 92 further from the heart. In this case, EGM sensing by distal electrodes may be retested at block 308 to ensure that the distal electrodes have not been moved to a location that is associated with a risk of cardiac capture. In one embodiment, only the most proximal pair of distal electrodes 90 is monitored to determine if an EGM signal can be sensed. If no EGM sensing is present on the most proximal pair of the distal electrodes, all of distal electrodes 90 may be presumed to be far enough from the patient heart to avoid cardiac capture. In another embodiment, the most distal electrode pair of electrodes 90 is tested. If at least the most distal pair does not sense an EGM signal, that most distal pair can be selected for right phrenic nerve stimulation.

In other embodiments, testing for capture of the heart or cardiac nerves by monitoring a heart rate using any available cardiac EGM or ECG signals may be performed in addition to, or alternatively to, monitoring for EGM sensing at blocks 308 and 310, during delivery of stimulation pulses using any of the distal electrodes 90 and/or proximal electrodes 92.

After at least one pair of proximal electrodes 92 and at least one pair of distal electrodes 90 are verified as not sensing an EGM signal or causing undesired cardiac capture, pre-stimulation thoracic impedance measurements are acquired at block 314 as previously described in conjunction with FIG. 5. One or both phrenic nerves may then be stimulated at block 316, e.g. using default supra-threshold stimulation parameters and a pair of electrodes verified to not be sensing an EGM signal or at least not capturing the heart or cardiac nerves.

The thoracic impedance measurement(s) are repeated at block 318 during stimulation (which may include measurements performed during and/or between pulse trains) to determine if an impedance measurement change due to stimulation meets some minimum expected threshold of improvement (block 320). If a threshold level of improvement is not reached, other stimulation parameters may be tested by adjusting the stimulation at block 326, using only electrodes known not to be sensing an EGM signal or causing a change in heart rate.

If a maximum number of attempts to improve the impedance measurement by stimulation parameter adjustment is reached, as determined at block 324, the lead position may need to be readjusted at block 312. In this case, and in other methods described herein where lead adjustment is performed, lead adjustment may include placing a new lead or leads having different dimensions and electrode configuration which may provide a better fit to the anatomy of an individual patient for successful transvenous phrenic nerve stimulation.

If the lead position is readjusted or a new lead is placed, the process returns to block 308. Testing for the presence of an EGM signal (and/or cardiac capture) using any of the distal electrodes 90 continues until the absence of an EGM signal and/or cardiac capture using at least selected ones of the proximal and distal electrodes 92 and 90 is verified and an acceptable improvement in the impedance measurement(s) is achieved.

Once an acceptable implantation site is identified based on the EGM and impedance signal testing, the lead may be fixed and coupled to IMD 10 to enable therapy delivery (block 322). If the testing described in conjunction with flow chart 300 is performed using a delivery and mapping catheter, the lead is advanced through the catheter, the catheter is withdrawn, and final verification of lead performance (i.e. absence of EGM sensing or cardiac capture using selected electrodes and adequate impedance measurement improvement) is performed and the lead is fixed in place.

Figure 8:
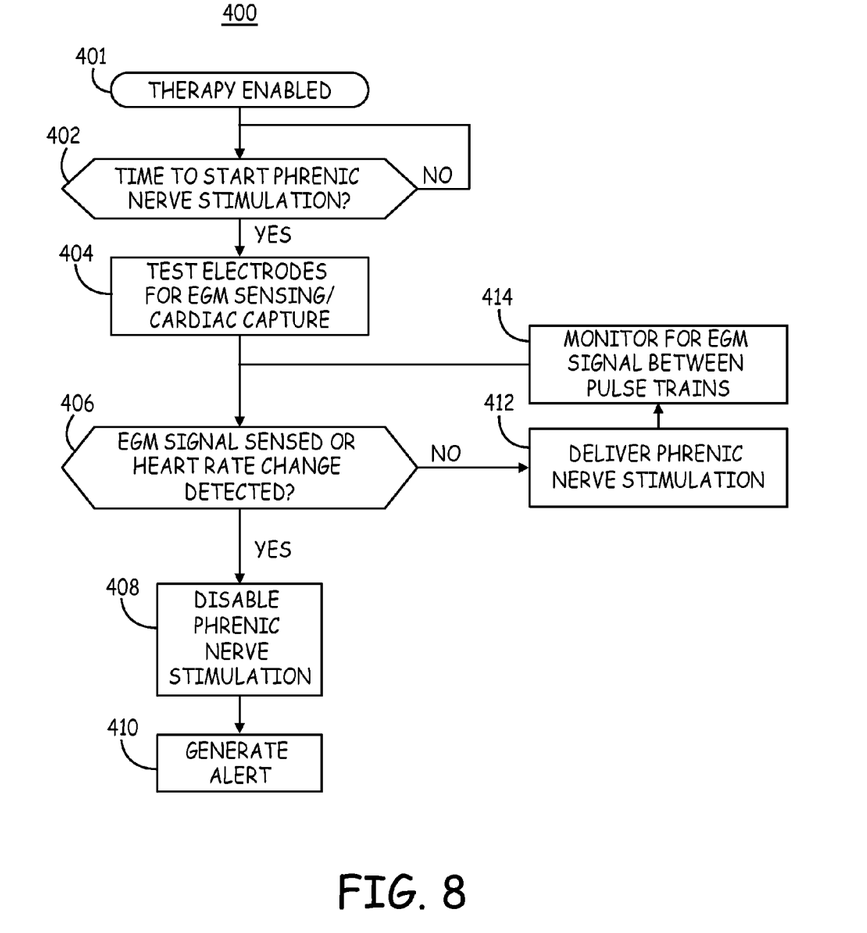
FIG. 8 is a flow chart of a method for delivering a phrenic nerve stimulation therapy according to one embodiment.

FIG. 8 is a flow chart 400 of a method for delivering a phrenic nerve stimulation therapy according to one embodiment. At block 401, phrenic nerve stimulation therapy is enabled. The nerve stimulation lead is positioned at a desired implant location using any of the methods described above, coupled to IMD 10, and the therapy is enabled according to a desired stimulation protocol for a given patient.

At block 402, a determination is made whether it is time to start phrenic nerve stimulation. In some embodiments, phrenic nerve stimulation is started immediately upon enabling the therapy. In other embodiments, stimulation may be scheduled to occur on a periodic basis, started upon a user command or user activation, or started in response to a change in another physiological signal monitored by the IMD.

If it is time to start phrenic nerve stimulation, the electrodes that are to be used for delivering stimulation pulses, which may be for right, left or both right and left nerve stimulation, are tested for EGM sensing and/or cardiac capture at block 404. Otherwise, the process continues to wait until it is time to start nerve stimulation as determined at block 402.

Testing of electrodes for EGM sensing at block 404 may involve selecting a test electrode pair via switching circuitry to couple the test pair to EGM sensing circuitry. The EGM sensing circuitry output is analyzed for regular sensed cardiac events and/or EGM morphology analysis is performed. One or more electrode pairs may be tested. Only the electrode pair that is known to be closest to the patients heart and selected for use for delivering nerve stimulation may be tested. For example, if right phrenic nerve stimulation is being achieved by electrodes positioned in the SVC (e.g. as in FIG. 2), only the electrode pair selected from the distal electrodes for right nerve stimulation is tested for EGM sensing. Any other more proximal electrodes and electrodes not selected for delivering stimulation pulses are not tested.

Testing at block 404 may additionally or alternatively include delivering single pulses, maximum pulse energy pulses, or other test stimulation pulses to selected test electrodes and monitoring for a change in heart rate as generally described above.

In some embodiments, electrodes known to be closest to the heart and electrodes to be used for stimulation are tested at block 404. Multiple electrode pairs may be tested for EGM sensing and/or cardiac capture in an automated, sequential or simultaneous manner using a multi-channel EGM sensing circuit.

If an EGM signal is sensed or a heart rate change during phrenic nerve stimulation is detected, as determined at block 406, phrenic nerve stimulation may be disabled at block 408. In other embodiments, if EGM sensing is present, as long as no cardiac capture is detected, phrenic nerve stimulation may still be delivered by advancing to block 412. If a change in heart rate due to inadvertent capture of the heart or a cardiac nerve during phrenic nerve stimulation is detected, phrenic nerve stimulation is disabled at block 408.

A patient alert signal may be generated at block 410 in response to disabling phrenic nerve stimulation. EGM sensing and/or cardiac capture by an electrode pair of the phrenic nerve stimulation lead indicates possible lead dislodgement, risk of inadvertent cardiac stimulation, and reduced effectiveness of phrenic nerve stimulation. An alert generated at block 410 notifies the patient or clinician that the lead position needs to be re-evaluated before phrenic nerve stimulation resumes. Phrenic nerve stimulation therapy may require manual re-enabling after being disabled due to EGM sensing.

In an alternative embodiment, if one electrode pair that is selected for nerve stimulation can sense an EGM signal or captures the heart or a cardiac nerve, other electrode pairs may be tested until one is found that does not capture the heart or a cardiac nerve. That pair may be used for nerve stimulation. Various factors will determine whether nerve stimulation therapy continues when one or more electrode pairs are found to sense an EGM signal and/or cause cardiac capture. Such factors include the patient's dependence on phrenic nerve stimulation for respiration, whether the patient has an implantable cardioverter defibrillator, and the relative distance of other electrodes available for nerve stimulation from electrodes sensing an EGM signal or causing a change in heart rate.

If no EGM sensing and/or heat rate change indicating capture of the heart or a cardiac nerve is detected at block 406, phrenic nerve stimulation is delivered as scheduled at block 412. Monitoring for an EGM signal and/or heart rate changes during nerve stimulation may be performed at block 414.

Switching circuitry or the use of blanking periods during stimulation pulse delivery may be used to allow for EGM sensing on electrodes used for nerve stimulation in between phrenic nerve stimulation pulse train delivery. Switching circuitry may be used to switch between coupling an electrode pair to EGM sensing circuitry and coupling an electrode pair to a pulse generator. Alternatively, a stimulation pair of electrodes may remain coupled to both a pulse generator and EGM sensing circuitry with blanking periods applied to the EGM sense amplifier during pulse train delivery.

If EGM sensing begins to occur or a change in heart rate is detected during therapy delivery (as determined at block 406), the nerve stimulation therapy may be disabled at block 408. If EGM signals are sensed, further testing checking for heart rate changes or R-wave morphology changes, to verify no capture of the heart or cardiac nerves is occurring may be performed using the same or other electrodes. If no evidence of cardiac capture is found, phrenic nerve stimulation may continue despite EGM sensing.

Thus, a method and apparatus for providing phrenic nerve stimulation therapy have been presented in the foregoing description with reference to specific embodiments. It is appreciated that various modifications to the referenced embodiments may be made without departing from the scope of the disclosure as set forth in the following claims.

The invention claimed is:

1. A method comprising:
  selecting a first bipolar pair of a plurality of electrodes in a first location for stimulating a nerve;
  in response to selecting the first bipolar pair, determining whether a cardiac signal can be sensed using the first bipolar pair as a sensing electrode pair, wherein determining whether the cardiac signal can be sensed occurs before delivery of stimulation to a nerve; and
    in response to not being able to sense a cardiac signal using the first bipolar pair, enabling stimulation of the nerve using the selected ones of the plurality of electrodes in the first location.

2. The method of claim 1, further comprising repositioning the plurality of electrodes to a second position for stimulation of the nerve in response to being able to sense a cardiac signal using the first bipolar pair.

3. The method of claim 1 further comprising:
  responsive to sensing the cardiac signal using the first bipolar pair, delivering a stimulation pulse to the nerve via the selected pair of the plurality of electrodes;
  monitoring the cardiac signal to detect a change in the cardiac signal in response to the stimulation pulse; and
  in response to no change in the cardiac signal being detected, enabling a nerve stimulation therapy to be delivered using the selected pair.

4. The method of claim 3 wherein detecting a change in the cardiac signal comprises detecting a change in heart rate.

5. The method of claim 1, wherein the plurality of electrodes comprises a distal set of electrodes positioned along a distal portion of a lead body and a proximal set of electrodes spaced proximally from the distal set of electrodes, each of the distal set and the proximal set comprising at least one electrode pair, the method further comprising selecting the first bipolar pair from the distal set of electrodes.

6. The method of claim 5 further comprising selecting a second bipolar pair of electrodes in response to sensing a cardiac signal using the first bipolar pair;
  determining whether a cardiac signal can be sensed using the second bipolar pair; and
  enabling stimulation of the nerve using a selected electrode pair of the plurality of electrodes in response to the determination.

7. The method of claim 6 wherein the distal set of electrodes comprises the first bipolar pair and the second bipolar pair.

8. The method of claim 5 wherein the proximal set of electrodes comprises a second bipolar pair of electrodes spaced at a distance from the distal set of electrodes of the lead, wherein the first location positions the second bipolar pair for stimulating a second nerve.

9. The method of claim 1, further comprising:
  introducing a lead comprising a lead body carrying the plurality of electrodes into a venous entry site;
  advancing the lead along the right innominate vein to position at least one pair of the plurality of electrodes for stimulation of a right phrenic nerve.

10. The method of claim 1, further comprising: introducing a lead comprising a lead body carrying the plurality of electrodes into a venous entry site; and
  advancing the lead along one of a superior vena cava and an inferior vena cava to position at least one pair of the plurality of electrodes for stimulation of a right phrenic nerve.

11. The method of claim 1, further comprising:
  delivering a nerve stimulation therapy in response to the enabling;
  monitoring for a change in heart rate during the nerve stimulation therapy; and
  disabling the nerve stimulation therapy in response to detecting a change in heart rate.

12. The method of claim 1, further comprising:
  selecting a second bipolar pair of the plurality electrodes; and
  switching from the first bipolar pair to the second bipolar pair during advancement of a lead carrying the first and second bipolar pairs to determine if the second bipolar pair is sensing an EGM signal.

13. The method of claim 1, further comprising scheduling nerve stimulation pulses to be delivered using an electrode pair selected from the plurality of electrodes;
  determining if an EGM signal is being sensed by the selected electrode pair; and
  disabling the nerve stimulation pulses in response to EGM sensing by the selected electrode pair.

14. A system comprising:
  means for selecting a first bipolar pair of a plurality of electrodes in a first location for stimulating a nerve;
  means for determining whether a cardiac signal can be sensed using the first bipolar pair as a sensing electrode pair, wherein determining whether the cardiac signal can be sensed occurs before delivery of stimulation to a nerve;
  means for enabling stimulation of the nerve using selected ones of the plurality of electrodes in the first location in response to not being able to sense a cardiac signal using the first bipolar pair; and
  means for repositioning the plurality of electrodes to a second position for stimulation of the nerve in response to being able to sense a cardiac signal using the first bipolar pair.

* * * * *